United States Patent [19]

Osipow et al.

[11] Patent Number: 4,726,944

[45] Date of Patent: Feb. 23, 1988

[54] INSTANT LATHERING SHAMPOO

[76] Inventors: Lloyd I. Osipow, 2 Fifth Ave., New York, N.Y. 10011; Dorothea C. Marra, 107 Fernwood Rd., Summit, N.J. 07901; J. George Spitzer, 44 Coconut Row, Palm Beach, Fla. 33480

[21] Appl. No.: 867,556

[22] Filed: May 28, 1986

[51] Int. Cl.$^4$ .......................... A61K 7/06; A61K 7/00; A61K 9/00

[52] U.S. Cl. .......................... 424/70; 424/47; 514/881

[58] Field of Search .................... 424/47, 70

[56] References Cited

U.S. PATENT DOCUMENTS

| 3,932,610 | 1/1976 | Rudy et al. | 424/70 |
| 4,213,960 | 7/1980 | Grollier et al. | 424/47 |
| 4,493,823 | 1/1985 | Möller et al. | 424/47 |
| 4,526,781 | 7/1985 | Goldberg et al. | 424/47 |

FOREIGN PATENT DOCUMENTS

| 1028957 | 4/1978 | Canada | 424/47 |
| 2717538 | 8/1978 | Fed. Rep. of Germany | 424/47 |

Primary Examiner—Jerome D. Goldberg
Assistant Examiner—F. Krosnick
Attorney, Agent, or Firm—Morgan & Finnegan

[57] ABSTRACT

Shampoo compositions are provided in unpressurized containers that generate a small, tight-bubbled lather more rapidly and more profusely than conventional shampoos, thereby improving the ease with which the shampoo is spread through the hair and rinsed away, resulting in more uniform cleansing. The compositions contain an aqueous solution of a water-soluble salt of lauryl sulfate, a volatile hydrocarbon or halogenated hydrocarbon boiling in the range of 25 C to 50 C, a tertiary amine oxide, and a sufficient amount of water-soluble gum to give the shampoo a viscosity in the range of about 1000 to 20,000 centistokes at 5 C.

8 Claims, No Drawings

INSTANT LATHERING SHAMPOO

BACKGROUND OF INVENTION

Shampoo compositions are available that are effective in cleansing the hair, provide copious lather, and have a creamy, lubricated feel. These compositions, which are available on the retail market, often employ as the primary surfactant a water-soluble salt of lauryl sulfate. Other detergents including the water-soluble salts of lauryl ethoxysulfate are also used as the primary or secondary surfactant.

In addition to water and these anionic surfactants, good shampoos invariably contain coco diethanolamide or lauroyl diethanolamide, which act both to stabilize the foam and to increase the viscosity of the composition. Often a small amount of an inorganic salt is added. This assists the diethanolamide in further increasing the viscosity, A water-soluble gum, particularly a cellulosic gum, may also be used to increase the viscosity. The viscosity of a shampoo should not be too low, otherwise the shampoo is likely to drip from the hair into the eyes.

Ancillary agents may include protein hydrolysates and fatty esters as hair conditioning agents. Preservatives, color and fragrance are also used.

In the past, conventional shampoos have been compounded with normally gaseous, liquified hydrocarbons or fluorocarbons, generally at vapor pressures in the range of 25 to 40 psig. These pressurized compositions delivered a pre-formed shampoo lather. However, there appeared not to be any benefit in the use of these products and they were not successful.

OBJECTS OF THE INVENTION

It is an object of the instant invention to provide shampoo compositions that have superior lathering properties. While shampoos are normally intended to produce ample lather, the compositions of the instant invention lather much more rapidly and with much less effort. Further, the volume and stability of the lather are greatly enhanced. As a consequence of the improved lathering qualities, the shampoo is more easily and more uniformly distributed throughout the hair and it is rinsed out more thoroughly. The more uniform distribution of the shampoo and the more thorough rinsing contribute to more uniform cleansing of the hair.

It is a further object to provide compositions that give shampoo lathers having a small, tight-bubbled structure, as distinguished from large, loose-bubbled, watery lathers. The extremely rapid formation of such fine, tight-bubbled lathers makes it unlikely that any shampoo will drip into the eye. In constrast, while the shampoo remains as a liquid, or if the lather is watery, it is prone to drip.

It is another object of this invention to leave the hair with good combability, i.e., the hair combs easily without snags and tangles.

It is an object of the invention to provide non-pressurized shampoo compositions with superior lathering qualities i.e., the vapor pressures of the shampoos are less than atmospheric pressure at ambient temperatures. Thus, the compositions may be packaged in unpressurized containers such as collapsible tubes, bottles, and bottles fitted with pumps.

DESCRIPTION OF THE INVENTION

To fulfill the objectives of this invention, it is not only necessary that the shampoo lather instantly and profusely, but the lather must be a small, tight-bubbled structure that has body and stays where placed, and it must be a stable lather. If the lather were composed of large, loose bubbles, or if the lather were unstable, it would be more prone to drip into the eyes. It is also necessary that the lather not be adversely affected by the soil present on the hair before cleaning. An additional requirement is that the shampoo leave the hair with good combing qualities, it should not snag or tangle, without the necessity for incorporating conditioning oils in the shampoo. Such conditioning oils depress the lathering qualities of the shampoo. In addition, they remain on the hair to collect dirt, and they tend to build-up with repeated use, causing the hair to droop. Another requirement is that the composition remain stable in its package, and not separate or deteriorate.

It has now been found that all of the requirements and objectives of this invention can be realized using a combination of four essential ingredients:

1. An anionic surfactant that is the primary foaming and cleansing agent selected from the group consisting of the water-soluble salts of lauryl sulfate. These may include ammonium, sodium, morpholine, and various alkanolamine salts, such as mono-, di-, and triethanolamine, mono-, di-, and triisopropanolamine, and 2-amino-2-methyl-1-propanol. The preferred anionic surfactant is ammonium lauryl sulfate.

A mixture of water-soluble salts of lauryl sulfate may be used as well as a single salt. Alternatively, a mixture of such salts of lauryl sulfate with other anionic surfactants or with amphoteric surfactants may be used. Preferred anionic surfactants that may be used in combination with lauryl sulfate are the water-soluble salts of lauryl ether sulfate containing from one to three ethoxy groups. Preferred amphoteric surfactants to use in combination with lauryl sulfate are lauric and myristic imidazolines and betaines.

The composition should contain from about 5 to about 20% by weight of anionic and amphoteric surfactants, of which the predominant surfactant should be a water-soluble salt of lauryl sulfate, preferably ammonium lauryl sulfate.

With less than about 5% of anionic and amphoteric surfactants present, the rate of lathering and the lather volume fall off substantially and the lathering qualities are more sensitive to soil present in the hair. With more than about 20% of these surfactants, lather volume and lather stability decrease.

2. In addition to the primary foaming agent, a gas-producing agent is also required. Voluminous gas production in the presence of a foaming agent can conceptually result in voluminous lather. The gas-producing agent used in the practice of the instant invention is selected from the class of volatile organic liquids boiling in the range of 25 C. to 50 C. at atmospheric pressure that comprise saturated hydrocarbons and halogenated hydrocarbons such as isopentane, n-pentane, 2-2-dimethyl-butane, and 1,1,2-trichlorotrifluoroethene. More volatile organic liquids or liquified gases can not be handled in conventional unpressurized containers without encountering excessive losses of the volatile ingredient; also, the composition is likely to be expelled as a lather rather than a liquid that is quickly worked into a lather. Less volatile organic liquids do not generate sufficient gas to be effective in producing a voluminous lather. The preferred volatile organic liquid is n-pentane.

If the volatile organic liquid is a saturated hydrocarbon it should be used at a concentration in the range of about 2 to about 10% by weight of the composition. If it is a halogenated hydrocarbon, it should be used at a concentration of about 4 to about 15% by weight of the composition. Lower concentrations do not provide sufficient foam enhancement, while higher concentrations tend to separate during storage and also tend to give a large and looser bubble structure.

3. It might be thought that the combination of a good foaming agent with a gas-producing agent, as described above, would be sufficient for the rapid production of a voluminous lather. It is not. With this combination, the effect of a gas-producing agent is barely noticeable. However, if a compatible water-soluble organic gum is combined with the composition in sufficient quantity to give a viscosity of at least about 1,000 centistokes at 5 C., a dramatic increase in foaming qualities is observed. The foam forms quickly and voluminously. It has been found necessary to employ sufficient water-soluble organic gum to give the composition a viscosity in the range of about 1,000 to about 20,000 centistokes at 5 C. If the viscosity is higher than this, the lather does not spread readily throughout the hair.

Depending on the organic gum, the required concentration can vary broadly, say from about 0.01% to about 10%. However, concentration is not the important factor, but the viscosity of the composition. In general, any water-soluble organic gum that is compatible with the composition and increases its viscosity sufficiently, may be used. These include cellulosic gums, such as methyl cellulose, hydroxypropyl methyl cellulose, hydroxybutyl methyl cellulose, hydroxyethyl cellulose, ethyl hydroxyethyl cellulose, and sodium carboxymethyl cellulose. Copolymers of acrylic acid and polyallyl sucrose may also be used. The preferred gums are selected from the group consisting of hydroxypropyl methyl cellulose and hydroxyethyl cellulose.

4. The fourth essential component of the shampoos of the instant invention is a non-ionic nitrogen-containing surfactant, particularly a tertiary amine oxide with one long hydrocarbon chain containing 12 to 14 carbon atoms, examples of which include lauryl dimethylamine oxide, myristyl dimethyl amine oxide, lauryl morpholine amine oxide, bis(2-hydroxyethyl)laurylamine oxide, and bis(2-hydroxyethyl)myristyl amine oxide. The addition of the tertiary amine oxide substantially increases the rate at which the lather forms, increases the lather volume, provides a smaller, more tight-bubbled lather that is less prone to drip, and after use, leaves the hair more compatible, with less tendency for snags and tangles.

Tertiary amine oxides are known to act as foam stabilizers with anionic surfactants and are considered to be comparable to the alkanolamides, such as lauryl diethanolamide. However, in the instant invention the alkanolamides do not behave the same. The lather forms more slowly, it is less voluminous, the bubble texture is larger and looser, and it does not impart the combability qualities to the hair.

The tertiary amine oxides should be used at a concentration in the range of about 0.3 to 3.0% of the composition. If too little is used, the lather does not form rapidly and it is less voluminous. If too much is used, the lather volume and lather stability are impaired.

In addition to the above four essential ingredients, the shampoo is compounded as a aqueous solution and various ancillary ingredients may be added. These include color, fragrance, sequestering agents, anti-dandruff agents, glossing agents and hair-conditioning agents.

Thus, the compositions of this invention are aqueous solutions containing:

| | |
|---|---|
| Anionic and amphoteric surfactants that are predominantly water-soluble salts of lauryl sulfate | about 5–20% |
| Nitrogen-containing non-ionic surfactant, particularly tertiary amine oxides having one long hydrocarbon chain with 12–14 carbon atoms | about 0.3–3% |
| Water-soluble gum | q.s. to about 1000–20,000 cs at 5C |
| Volatile organic liquid, B.P. 25–50 C at atmos. pressure | |
| if hydrocarbon | about 2–10% |
| if halogenated hydrocarbon | about 4–15% |

A variety of subjective and objective tests were conducted to evaluate shampoo compositions, as follows, (a) A drop of shampoo was placed on a clean glass surface and observed as the lather developed with regard to bubble size and the looseness of the lather.

(b) The experimenter washed his or her wet arms with the shampoo and observed how quickly the lather developed, the lather volume, and the firmness of the lather.

(c) Subjects washed their hair and reported the results of their observations.

(d) A standardized procedure was used to develop a lather to determine the time required for the lather to develop and the density of the lather after working. A foamed polystryene sheet with rough surfaces, 8.5 inches on one side, was wet with warm water. From 1.5 to 2.0 grams of shampoo was placed in the center of the sheet and the shampoo was rubbed in a circular motion with a plastic cup 1.1 inches in diameter with a rough surface. After a predetermined period of time, the lather was transferred to a measuring cup and its density determined. While rubbing the shampoo, the time required for a shampoo lather to form was determined.

(e) The ability of the shampoo to lather in the presence of soil was determined using the same procedure as in (d) with the following modifications: After wetting the plastic sheet with warm water, 0.2 g of corn oil was placed in the center of the sheet, and 2.0 g of shampoo was placed on the oil. The lather was developed by rubbing for 60 seconds, and then the lather density was determined.

(f) The viscosity of the shampoos were determined using a Brookfield Viscosimeter. The shampoos were first chilled to 5 C. to avoid formation of gas bubbles, which could occur at higher temperatures, leading to incorrect results.

The following Series 1 shows the effect of the various ingredients on the foaming qualities of the shampoo.

| | Parts By Weight | | | | | | |
|---|---|---|---|---|---|---|---|
| | 1A | 1B | 1C | 1D | 1E | 1F | 1G |
| Ammonium Lauryl sulfate | 10.9 | 7.8 | 7.2 | 5.9 | 7.2 | 5.9 | 7.8 |
| Lauryl dimethyl amine oxide | — | 1.3 | — | 1.3 | — | 1.3 | 1.3 |
| Lauryl diethanolamide | — | — | 1.9 | 1.9 | 1.9 | 1.9 | — |
| Hydroxy- | — | — | — | — | 2.2 | 2.2 | 3.5 |

-continued

|  | Parts By Weight | | | | | | |
| --- | --- | --- | --- | --- | --- | --- | --- |
|  | 1A | 1B | 1C | 1D | 1E | 1F | 1G |
| propyl methyl cellulose |  |  |  |  |  |  |  |
| n-Pentane | 3.8 | 3.8 | 3.8 | 3.8 | 3.8 | 3.8 | 3.8 |
| Water q.s. | 100 | 100 | 100 | 100 | 100 | 100 | 100 |
| Time required to lather, sec. (1) | >30 | >30 | >30 | >30 | >30 | >30 | <10 |
| Foam volume, (1) c.c./gm after |  |  |  |  |  |  |  |
| 30 sec | — | — | — | — | — | — | 8.3 |
| 60 sec | 2.6 | 3.3 | 4.0 | 5.0 | 5.0 | 5.0 | 7.2 |
| Viscosity at 5C, cs (2) | <100 | <100 | <100 | <100 | 900 | 800 | 2,800 |

(1) Procedure (d) above;
(2) Procedure (f) above
Note that Foam Volume is the Inverse of density
Lather Quality
1A large, loose bubbles
1B large, loose bubbles
1C large, loose bubbles
1D large, loose bubbles
1E large, loose bubbles
1F large, loose bubbles
1G small, tight bubbles It can be seen that the combination of ammonium lauryl sulfate with n-pentane does not produce a rapid, voluminous lather with small, tight bubbles. The addition of a foam stabilizer does not help significantly. It is not until there is a sufficient increase in the viscosity of the shampoo using a compatible water-soluble gum that the required lather is obtained.

Series 2 shows the effect of increasing the concentrations of foam stabilizers, as well as the effect of further increases in the concentration of the organic gum.

|  | 2A | 2B | 2C | 2D | 2E | 2F | 1G |
| --- | --- | --- | --- | --- | --- | --- | --- |
| Ammonium lauryl sulfate | 9.1 | 8.5 | 7.8 | 7.8 | 7.8 | 7.8 | 7.8 |
| Lauryl dimethyl amine oxide | — | 0.7 | 2.0 | — | — | — | 1.3 |
| Lauroyl diethanolamide | — | — | — | 1.9 | 3.3 | 5.2 | — |
| Hydroxyproply methyl cellulose | 3.5 | 3.5 | 3.5 | 3.5 | 3.5 | 3.5 | 4.8 |
| n-pentane | 3.8 | 3.8 | 3.8 | 3.8 | 3.8 | 3.8 | 3.8 |
| Water q.c. | 100 | 100 | 100 | 100 | 100 | 100 | 100 |

|  | 2A | 2B | 2C | 2D | 2E | 2F | 2G |
| --- | --- | --- | --- | --- | --- | --- | --- |
| Viscosity at 5C (2) | 2,400 | 7,000 | 1,800 | 5,500 | 2,400 | 1,700 | 100,000 |
| Time required to lather, sec. (1) | 10 | 10 | 10 | 10 | 10 | 10 | 10 |
| Foam volume, cc/gm after |  |  |  |  |  |  |  |
| 30 sec. (1) | 6.7 | 7.7 | 9.1 | 7.1 | 8.8 | 5.3 | 10.0 |
| 60 sec. (1) | 6.7 | 7.7 | 7.1 | 8.3 | 6.2 | 4.8 | 7.7 |

(1) Procedure (d) above;
(2) Procedure (f) above

Comparing 2F with 2D and 2E, it can be seen that too much diethanolamide causes the lather volume to fall off. 2A without any nitrogen-containing nonionic surfactant gives smaller lather volume than 2B, 2C, 2D, 2E, and 2G.

Procedures (a), (b) and (d) led to additional observations. Comparing 2A with 2B, they showed that 2A developed its lather more slowly, gave a smaller lather volume, gave a coarser bubble texture, and had poor lather lubricity. Sample 2C has more amine oxide than 2B. Comparison of the two showed that 2C developed its lather faster and produced a larger volume of lather. Samples 2D, 2E and 2F, with alkanolamide, have looser bubble texture than those with amine oxide, and they build foam volume more slowly. Sample 2G, with a much higher viscosity, develops a high foam volume quickly, but it is difficult to spread on the hair and then rinse away.

It might be thought that conventional shampoos could be given the lathering qualities of the compositions of the instant invention, simply by the addition of a suitable volatile liquid. To test this, a number of shampoos were selected at random and combined with n-pentane in the proportion of 96 parts by weight of shampoo to 4 parts by weight of n-pentane. The shampoos selected are listed below, along with their principal ingredients in decreasing order. Water and ancillary ingredients are not listed.

| Prell for Normal and Dry Hair ammonium lauryl sulfate, cocoyl diethanolamide, hydroxypropyl methyl cellulose. | Procter and Gamble |
| --- | --- |
| Enhance Shampoo Normal Hair ammonium lauryl sulfate, ammonium laurethoxy sulfate, lauryl diethanolamide. | S.C. Johnson |
| Clairol Conditioner Shampoo Extra Body Formula sodium laurethoxy sulfate, lauryl diethanolamide | Clairol |
| For Oily Hair Only ammonium lauryl sulfate, cocamidopropyl betaine | Gillette |
| VO 5 Normal Hair sodium lauryl sulfate, lauryl diethanolamide, hydroxypropyl methyl cellulose | Alberto-Culver |

Listed below are viscosities at 5 C. before and after incorporating n-pentane, and the lather volume and appearance (with n-pentane) using procedure (d). Without pentane, lather volumes did not exceed 1.5 c.c./gm by this procedure.

|  | Prell | Enhance | Clairol | Gillette | VO5 |
| --- | --- | --- | --- | --- | --- |
| Viscosity, cs without pentane | 1,000,000 | 150,000 | 30,000 | 25,000 | 100,000 |
| Viscosity, cs with pentane | 100,000 | 1,000 | 750 | 900 | 800 |
| Lather volume with pentane |  |  |  |  |  |
| c.c/gm after 30 sec. | 5.5 | 4.3 | — | 5.3 | 5.9 |
| c.c./gm after 60 sec. | 5.0 | 5.3 | 4.8 | 5.3 | 6.2 |
| Appearance of lather after 30 sec. | shampoo lather | watery lather | no lather | watery lather | watery lather |
| Appearance of lather after 60 sec. | shampoo lather | shampoo lather | watery lather | shampoo lather | shampoo lather |

None of the conventional shampoos tested after the addition of n-pentane had the viscosity required by the instant invention. All gave watery lathers after 30 seconds, except Prell, and with Prell the lather volume was only about two-thirds of that obtained with the compositions of the instant invention.

Comparisons by Procedures (b) and (c) show the modified Prell to develop a lather substantially more slowly and achieve less than one-half the lather volume as the compositions of the instant invention.

The following examples illustrate the invention. The compositions may be packaged in collapsible tubes, or in bottles fitted with pumps or from which the contents may be poured.

EXAMPLES 1 AND 2

These examples illustrate the effect of increasing the concentration of ammonium lauryl sulfate, lauryl dimetyl amine oxide and n-pentane on performance.

|  | Parts By Weight | |
| --- | --- | --- |
| Examples | 1 | 2 |
| Ammonium lauryl sulfate | 7.8 | 11.3 |
| Lauryl dimethyl amine oxide | 1.4 | 2.0 |
| Hydroxypropyl methyl cellulose | 3.5 | 3.4 |
| Water | 83.5 | 77.6 |
| n-pentane | 3.8 | 5.7 |

The pentane is withheld and the shampoo is prepared in a customary manner. One procedure is to first prepare a 10% solution of the gum by dispersing the powdered gum in hot water and then mixing with ice-cold water to dissolve the gum. The lauryl sulfate and the amine oxide are usually supplied as 30% solutions. These are combined with the gum solution and water at room temperature. Preservatives, color, fragrance and other special function ingredients, according to preference, are incorporated in the shampoo, which is then cooled to below 10 C., and the n-pentane is mixed in. The compositions are then packaged. The results that follow are for the compositions without ancillary ingredients.

| Examples | 1 | 2 |
| --- | --- | --- |
| Viscosity at 5C, cs, (f) | 2,100 | 1,800 |
| Lather volume, after 30 sec., cc/g (d) | 11.1 | 11.1 |
| Lather volume, after 60 sec., cc/g (d) | 8.3 | 10.0 |
| Lather volume, with soil present, cc/g (e) | 5.5 | 7.7 |

( ) test procedure

Using procedures a, b and c, both examples were found to give voluminous lathers rapidly. Lathers were composed of small, tight bubbles. Both examples left the hair feeling soft and easily combed without snags and tangles.

EXAMPLES 3, 4 AND 5

These examples illustrate the use of mixtures of anionic surfactants as well as the use of myristyl dimethyl amine oxide.

|  | Parts By Weight | | |
| --- | --- | --- | --- |
| Example | 3 | 4 | 5 |
| Ammonium lauryl sulfate | 9.4 | 6.3 | 6.3 |
| Sodium lauryl sulfate | — | 3.3 | — |
| Sodium laurylethoxy (1) sulfate | — | — | 3.3 |
| Lauryl dimethyl amine oxide | — | 1.7 | 1.7 |
| Myristyl dimethyl amine oxide | 1.7 | — | — |
| Hydroxypropyl methyl cellulose | 3.4 | 3.4 | 3.4 |
| water | 80.7 | 80.5 | 80.5 |
| n-pentane | 4.8 | 4.8 | 4.8 |

The gum solution is prepared as previously described and combined with aqueous solutions of the anionic surfactants and amine oxides, and water at room temperature. Ancillary ingredients are added according to preference. The shampoo is then cooled to below 10 C. and the n-pentane is mixed in. The shampoos are then packaged. The results that follow are for the compositions without ancillary ingredients.

| Example | 3 | 4 | 5 |
| --- | --- | --- | --- |
| Viscosity at 5C, cs, (f) | 2,000 | 2,300 | 1,500 |
| Lather volume, after 30 sec., cc/g (d) | 7.7 | 12.5 | 12.5 |
| Lather volume, after 60 sec., cc/g (d) | 6.7 | 9.1 | 9.1 |
| Lather volume, with soil present cc/g (e) | 3.7 | 8.3 | 9.1 |

All three examples were found to give voluminous small, tight-bubbled lathers rapidly, and all left the hair feeling soft and easily combed, without snags and tangles, using procedures a, b, and c. From the above procedures d and e, it can be seen that these mixtures of anionic surfactants are particularly effective in giving high lather volumes, particularly in the presence of soil. A comparison of Example 3 with Examples 1 and 2 indicate that myristyl dimethyl amine oxide is less effective than the lauryl derivative in giving high foam volumes, particularly with soil present.

What is claimed is:

1. A shampoo that is essentially without liquified propellants and that is poured or otherwise expelled from its container as a viscous liquid that rapidly generates a small, tight-bubbled, voluminous lather consisting essentially of an aqueous solution of (1) water soluble salts of a lauryl sulfate surfactant in an amount of about 5 to 20% by weight of the total composition, (2) a nitrogen containing non-ionic surfactant in amount from about 0.3 to 3% by weight of the total composition, (3) a volatile hydrocarbon or halogenated hydrocarbon boiling in the range of 25° C. to 50° C. at atmospheric pressure in an amount of about 2 to 15% by weight of the total composition, and (4) a compatible water-soluble gum in sufficient quantity to give the shampoo a viscosity in the range of about 1000 to 20,000 centistokes at 5° C.

2. A shampoo according to claim 1 wherein part of the water soluble salt of lauryl sulfate is replaced by a different anionic surfactant or amphoteric surfactant but wherein said water soluble salt of lauryl sulfate is the predominant surfactant in (1).

3. A shampoo according to claim 1 wherein the nitrogen containing non-ionic surfactant is lauryl amine oxide.

4. A shampoo packaged in an unpressurized container that is an aqueous solution containing water-soluble salts of a lauryl sulfate surfactant in an amount of about 5 to 20% by weight of the total composition, a tertiary amine oxide with a long hydrocarbon chain having 12 to 14 carbon atoms in an amount of about 0.3 to 3% by weight of the total composition, a volatile hydrocarbon or halogenated hydrocarbon boiling in the range of 25° C. to 50° C. at atmospheric pressure in the amount of about 2 to 15% by weight of the total compositions, and a sufficient quantity of a compatible water-soluble gum to give the shampoo a viscosity in the range of about 1000 to 20,000 centistokes at 5° C.

5. A shampoo according to claim 1 or 4 wherein the water-soluble salt of lauryl sulfate is ammonium sulfate.

6. A shampoo according to claim 4 wherein the tertiary amine oxide is lauryl dimethyl amine oxide.

7. A shampoo according to claim 1 or 4 wherein the volatile hydrocarbon or halogenated hydrocarbon is n-pentane.

8. A shampoo according to claim 1 or 4 wherein the compatible water-soluble gum is a cellulosic gum.

* * * * *